United States Patent [19]
Wandrey et al.

[11] Patent Number: 5,906,940
[45] Date of Patent: *May 25, 1999

[54] CULTURING CELLS ON MACROPOROUS GLASS CARRIERS COATED WITH GELATIN, EXTRACELLULAR MATRIX PROTEIN AND STROMAL CELLS

[75] Inventors: Christian Wandrey; Manfred Biselli; Bernd Schröder, all of Jülich, Germany; Hans-Joachim Schmoll, Hanover, all of Germany

[73] Assignee: Forschungszentrum Julich GmbH, Julich, Germany

[ * ] Notice: This patent is subject to a terminal disclaimer.

[21] Appl. No.: 08/602,137

[22] Filed: Feb. 15, 1996

[30] Foreign Application Priority Data

Feb. 16, 1995 [DE] Germany .............. 195 05 109

[51] Int. Cl.$^6$ .............. C12N 5/06; C12N 5/08; C12N 11/14; C12N 11/02
[52] U.S. Cl. .......... 435/402; 435/176; 435/177; 435/395; 435/403; 435/289.1
[58] Field of Search .................. 435/174, 176, 435/177, 180, 240.23, 240.24, 240.243, 287.1, 395, 402, 403, 289.1

[56] References Cited

U.S. PATENT DOCUMENTS

| | | | |
|---|---|---|---|
| 5,041,138 | 8/1991 | Vacanti et al. | 623/16 |
| 5,443,950 | 8/1995 | Naughton et al. | 435/1 |
| 5,601,757 | 2/1997 | Biselli et al. | 261/122.1 |

OTHER PUBLICATIONS

Kratje, et al., Biotechnol. Bioeng., vol. 39, pp. 233–242 (1992).
Kratje, et al., Biotechnol. Prog., vol. 10, pp. 410–420 (1994).

*Primary Examiner*—David M. Naff
*Attorney, Agent, or Firm*—Herbert Dubno; Jonathan Myers

[57] ABSTRACT

Stem cells or other organ-function cells are cultivated in a fluidized bed system on macroporous glass carrier bodies treated with a structure protein such as gelatin and an extracellular matrix protein such as fibronectin, and coated with a stroma cell layer. Glass carriers coated with gelatin are added to a fluidized bed reactor, and a culture medium containing an extracellular matrix protein is added to bind the protein to the gelatin. Stromal cells are then added and the cells are cultured to immobilize the cells on the carriers containing the bound protein. Immature organ-function cells are added to the reactor, and while generating a fluidized bed of the carriers in the culture medium, the culture medium is recirculated from and to the reactor in a recirculation loop. Bubble-free aeration of the culture medium is effected to cultivate the immature organ-function cells on the carriers to obtain both mature differentiated organ-function cells and progenitor organ-function cells. Mature differentiated organ-function cells which are released from the carriers are harvested from the reactor while retaining the progenitor organ-function cells which adhere to the carriers to provide an equilibrium between the harvested mature differentiated organ-function cells, the progenitor cells and the immature cells added to the reactor. Growth and regulatory factors for cultivating organ-function cells can be produced by culturing immobilized stromal cells in the reactor in the absence of the organ-function cells.

17 Claims, 6 Drawing Sheets

CULTURING CELLS ON MACROPOROUS GLASS CARRIERS COATED WITH GELATIN, EXTRACELLULAR MATRIX PROTEIN AND STROMAL CELLS

FIELD OF THE INVENTION

The present invention relates to the cultivation of organ-function cells of human and other animal organisms and, more particularly, to a process for the cultivation of human or animal organ-function cells which can be colonized on porous microcarriers and on which the cultivation can be carried out by supplying the cells continuously with a growth medium.

The invention also relates to microporous glass carrier suitable for this purpose and to a cell-cultivation apparatus using the carriers.

BACKGROUND OF THE INVENTION

The ex vivo cultivation of aspirated organ-function cells or of cells with a partial organ function, like human tissue, bone marrow, liver cells and skin cells, is of great interest in the medicinal, therapeutical and pharmaceutical and research and development fields. For example, various clinical treatments utilize bone marrow, umbilical cord blood or blood recovered from peripheral stem cells.

Of special interest is the field of leukemia treatment for which the cultivation of bone marrow stem cells is important for increasing or at least maintaining levels of such cells in the treated organism or maintaining equilibria involving same so as to overcome the donor problem, problems of acceptance of foreign cells, rejection, etc. In the past, efforts have been made to overcome these problems in various ways.

For example in an autologous bone marrow transplant techniques, bone marrow is removed from the patient/recipient and returned to the patient after, for instance, cancer therapy.

In the future, therapy is considered in which the leukemic or tumor infiltrated bone marrow is expected to be subjected externally of the patient to a treatment or healing and then returned to the patient (ex vivo purging).

In allogenic bone marrow transplant techniques, the healthy bone marrow of a donor is administered to the leukemic patient from whom bone marrow has been removed. Complications can arise here in that the foreign bone marrow can be rejected or can treat the tissue of the patient/recipient as foreign tissue and attack it (graft vs. host reaction).

In the past, in practically all cases bone marrow had been transplanted only as a cell mixture. More recently, however, the stem cells are recovered from the bone marrow by the administration of cytokines in a process in which the cytokines mobilize the stem cells in the peripheral blood. These stem cells are purified immunologically and then transplanted to the patient. The need for the removal of bone marrow from a donor is thus eliminated along with the pain and stress on the body with which the bone marrow extraction has been associated. In the stem cell recovery procedure, only the desired stem cells are removed and the remaining cells are returned to the donor so that the loss of hemapoietic cells is a minimum for the donor.

A process for increasing or at least maintaining the concentration of such organ-function cells is important for all of the more recent treatment techniques as described above. The maintenance or cell-increasing cultivation of progenitor cells, (bone marrow stem cells) is expressly important for the production of blood cells for blood transfusions, to replace donor blood, from autologous cells from a patient himself or herself or for donor stem cells for allogenic transfusions and wherever mature blood cells are required. The latter can be utilized in transfusions requiring erythrocytes, thrombocytes and granulocytes. This can greatly reduce the danger of infection for the blood recipient greatly or eliminate it entirely and can insure a uniform product quality.

Furthermore, with cultivation of organ-function cells yielding an increase in the cells, a donor bank can be established in which all of the required specific stem cells for a transplant can be held in readiness. This can reduce the enormous expense and time pressure which can arise at the time that an organ-cell transplant is required.

For over 10 years efforts have been made to cultivate organ-function cells and mixed population cells derived from tissue. However, true long term cultures have been found to be extraordinarily problematical.

From EP 0 241 578 A1, for example, it has been proposed to cultivate bone marrow preparations, especially hemapoietic stem cells, on stroma or fiberblasts which initially have been cultured on a network especially of nylon before being inoculated with the hemapoietic cells.

According to EP 0 358 506 A1, carriers of optional configuration can be suspended in a growth medium and the culture can be carried out with periodic medium replacement.

In WO 92/21402, the ex vivo cultivation of hemapoietic precursor cells is carried out with a prior treatment or in the presence of growth factors or cytokines.

From WO 93/18136, the cultivation of hemapoietic cells on microcarrier beads is taught with continuous or intermittent growth medium supply, the process being carried out in a stirred reaction vessel or airlift bioreactor. Described here is the cultivation of cells which are grown on collagen in spinner flasks.

Finally, T.-Y. WANG et al u.a. (Ann. NY. Acad Sci. 1990, Pages 274–284) describe a three-chamber apparatus for the culturing of hemapoietic cells which are grown on highly porous collagen microspheres. The latter are provided as a packing in the intermediate chamber and the packing is separated from the chambers traversed by the growth medium by a perfusion membrane.

Even these techniques do not result in a true long term cultivation of organ-function cells.

OBJECTS OF THE INVENTION

It is the principal object of the present invention to provide an improved process which enables a replication of organ-function cells, especially stem cells, to a degree that losses as a result of out differentiation are compensated or limited, i.e. the increasing disappearance of the cell line which has been observed to date the death of the culture, can be avoided and, if possible, a significant excess can be repeatedly harvested.

Another object of the invention is to overcome drawbacks of earlier systems for the cultivation of organ-function cells.

It is also an object to provide an improved apparatus for cultivating cells.

Still another object is to provide an improved support for cell cultivation.

SUMMARY OF THE INVENTION

The invention, while finding its greatest interest for the replication of bone marrow stem cells, with which the balance of this description is largely concerned, is not, however, limited to the cultivation of such cells but rather can be utilized for the cultivation of other organ-function cells or mixed cell populations including without limitation:

liver cells with liver stem cells, hepatocytes, copper star cells as organ-function cells;

thyroid cells with epithelial cells and perifollicular cells as the organ-function cells;

cartilage cells where chondrocytes are the function cells; and bone with osteoblasts and osteoclasts as the function cells. All such cells can be grown for long periods with an increase in the cell population or at least a stable or constant cell population allowing harvesting of the grown cells.

According to the invention, the cultivation is carried out in a fluidized bed reactor having a recirculation cycle with bubble-free aeration in the reactor itself or in the recirculation cycle utilizing a support consisting of macroporous glass carriers of a maximum of 1500 $\mu$m diameter coated with a stromal cell layer and provided with a structure protein or structure protein hydrolyzate coating and preferably also coated with extracellular matrix protein.

According to a feature of the invention, the carrier, coated with gelatin and pretreated with fibronectin, is enriched with stroma cells before being seeded or inoculated with the organ-function cells.

According to this aspect of the invention the preculture is carried out with bone marrow stroma cells and as organ-function cells, peripheral stem cells or bone marrow are used.

The pretreatment with fibronectin can be effected by treating the carriers in the reactor with a medium containing calf serum.

The carriers are preferably glass beads with a diameter of 400 to 700 $\mu$m, a carrier porosity of 50% and a pore size of 30 to 150 $\mu$m.

The proportion of interstitial volume of the particles in the fluidized bed to the total fluidized bed volume amounts to 50 to 75% (fluidized bed porosity) and is achieved with a carrier proportion in the fluidized bed of 20 to 60% (i.e. the carrier volume) makes up 20 to 60% of the working volume of the reactor including the recycling circuit. The carrier volume can be the piled volume of the carriers.

According to a feature of the invention the medium supply can be continuous and has a residence time below 72 hours, amounting especially to 10 to 50 hours.

The carrier growth in the reactor can be monitored by a biomass probe effecting a capacitance measurement and whose information (signal) is used as the control parameter for the cell count and thus for the medium supply. The cultivation can be used to generate organ simulates and advantageously liver or bone marrow function cells are produced in long term cultures.

The process can be used to generate mature blood cells through an immobilized hemapoietic system.

The process which has been described can be carried out without organ-function cells with the culture being that of stromal cells from which regulation factors are recovered from the harvested medium. The apparatus can be provided with means for the sterile removal of the carriers from the fluidized bed reactor.

It has been proposed more than 10 years ago (DE OS 3 410 650) to carry out cell cultivation in fluidized bed reactors with macroporous glass bodies and to effect cell cultures with bubble-free aeration (see, for example, D. Looby, J. B. Griffiths: "Animal cell technology"; Pages 336–344, Butterworth-Heinemann 1988). However, these techniques were found to be only suitable for cell lines without organ function, e.g. for synthetic protein production. Indeed, efforts to carry out organ-function cell reproductions in such systems have been found to be fruitless.

It was only with the advent of the treatment of large pore glass carriers, especially glass carriers with macropores and micropores, utilizing a technique of the type taught in DE-OS 28 29 580, that it has been possible to effectively carry out long term culturing of organ-function cells without the drawbacks of earlier systems. The coating technique described in this latter patent publication was used on particles of a very small size which were not, however, suitable for fluidized bed reactors of the type with which the invention is carried out.

The macroporous glass particles of the invention are provided with a thin layer of structure protein or a structure protein hydrolysate, for example, gelatin and treated with extra cellular matrix protein like fibronectin, laminin, heparin sulfate or the like and then coated with stroma cells. With this system there is an increase in the cell production and an increase in the cell mass when organ cells are cultured in the fluidized bed on these carriers.

The macroporosity and limited particle size of the carriers appear to play an important role. Apparently they are critical to the nesting of cellular material in the carriers and communication of the cellular material with the ambient medium, precluding accumulation sites for barrier materials or decomposition products. Such barrier systems and decomposition productions are thus in a diffusion equilibrium with a medium which insures that the growth medium in its optimum concentration will continuously contact the carriers.

The flow velocity of the growth medium is relatively small and the carriers tend to remain fluid in the reactor and not be washed out of the latter so that no significant shear stress is applied to the cell growth on the carriers. By continuous medium replacement, out differentiated cells are mobilized in the flowing medium and carried out of the reactor into the product vessel. The equilibrium between immature and mature cells which is required for the self sustaining equilibrium of the stem cells is thus maintained.

The growth and regulation factors provided by the stroma cells are retained in the culture regions of the carriers because of the high pore diameter and thus the titers of these agents are not cut by the nutrient medium and thus are concentrated where they are required for stem cell culturing and multiplication.

The carrier size should lie in the range of 200 to 1500 $\mu$m with the choice of the particle size of the glass carriers being determined by the flow conditions which are to be maintained in the fluidized bed. The fluidization in the bed should not be so intensive that the deposition of the organ-function cells in the hollow carriers is disturbed. In general, it is desirable that the flow conditions in the fluidized bed approximate physiological flow conditions which is less to be feared with carriers of the invention than with larger carriers.

The pores of the large-pore carriers should be large enough to provide the space required for colonization of the cell population and thus can scarcely be smaller than 10 to 20 $\mu$m, since aspirated cells are larger than 10 $\mu$m. The porosity of the glass carriers should be as high as possible with a minimum of 40% and the open pores should have pore sizes up to and in excess of 100 $\mu$m for best results. A preferred pore size for the glass carriers is 30 to 120 microus.

Especially suitable and desirable are carriers with a particle size of 400 to 700 $\mu$m and a pore size of the order of 50 μm, the glass particles having a density in the range of 1.1 to 1.8 Kg/liter (measured with water filled pores). The results which are desirable with the present invention can also be obtained with somewhat larger carriers (up to a particle size of 1500 μm) which can have limited colonization inhibitors limiting access to interior regions of the body, e.g. by sealing cell layers.

The thin layers of structure protein or protein hydrolyzate applied to the glass form with the bound matrix proteins like, for example fibronectin, bond promoters between the glass and the cultured cells. The layers containing gelatin can be obtained, for example, by treating the highly cleaned glass particles with water-free gelatin solutions.

A matrix protein coating, for example a fibronectin coating, can be generated by treating the glass beads previously coated with the gelatin or some other structure protein or structure protein hydrolyzate, with a medium containing serum. The matrix protein can also be applied in pure form to the carriers to be coated with the matrix protein coating.

For depositing stromal cells on the thus treated surface of the glass particles, it is preferred to use a preculturing of stroma cells on the surface of the glass carriers at the slowest possible flow velocity during which an osmolarity of 300 mOsml can be established and the medium supply is interrupted for 3 to 5 hours. The stromal cell layer on the carriers serves to provide the requisite adhesivity for the organ-function cells. For inoculating the coated carriers, the organ-function cells are taken up in fresh growth medium and thus form a suspension which is fed to the reactor. Within about two hours, the organ-function cells adhere to the carriers and thus can be maintained in a viable and active form for very long periods of time.

The product released into the medium, namely, reproduced cells, cell mixtures or protein, can be continuously or discontinuously harvested or the organ-function cells can be recovered by passing quantities of the growing cells on the carriers or support through a gate in the system and releasing the cells from the support. The growth and regulatory factors which are released by stromal cells are recovered analogously without colonizing the carriers with the organ-function cells.

Carriers which are coated with structure protein or additionally with matrix proteins and also have been colonized with stromal cells can be prepared in sterile form and utilized for test purposes, research purposes or production purposes.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
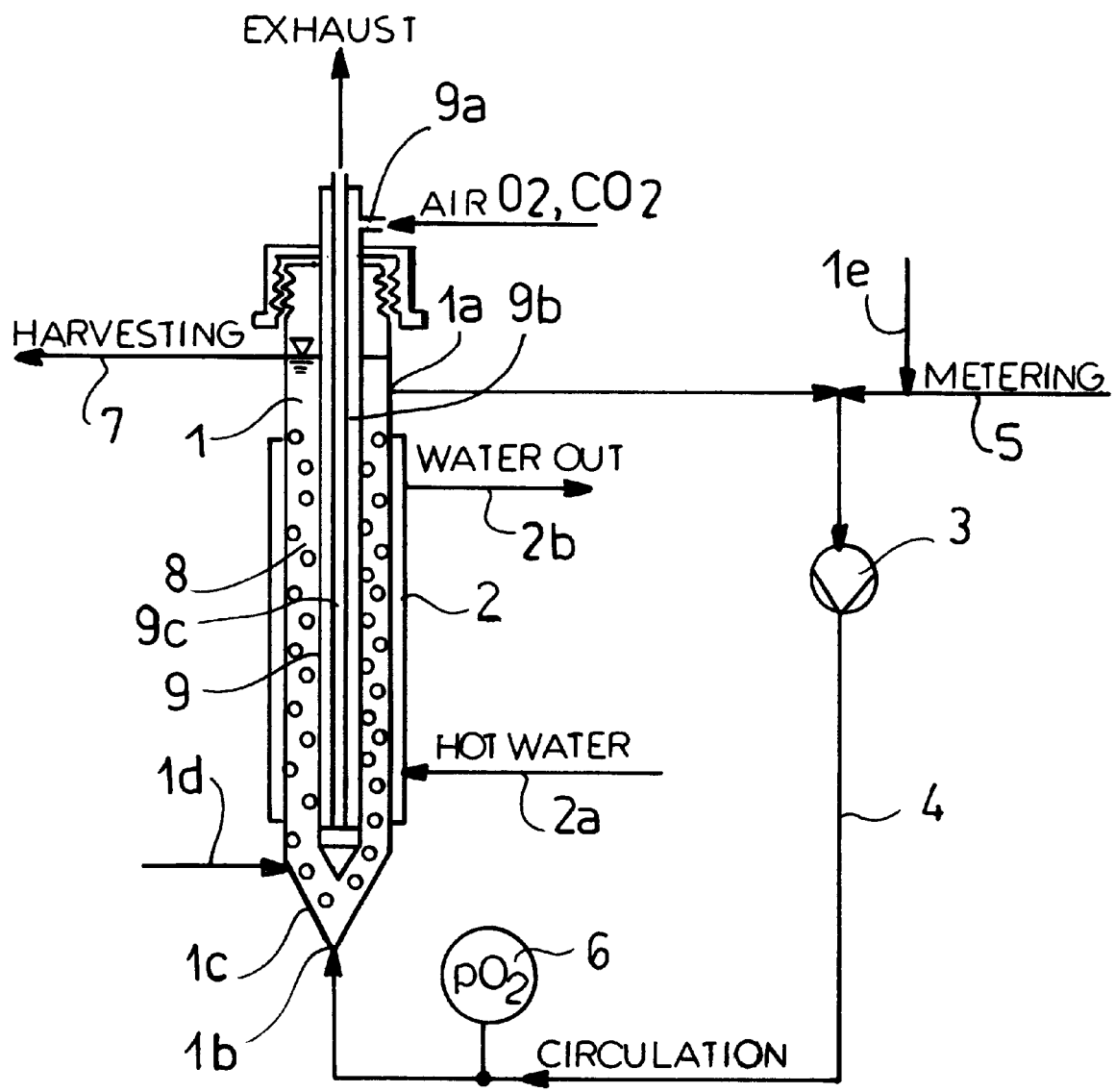
FIG. 1 is a diagram of an apparatus for carrying out the process of the invention.

FIG. 1 shows a reactor 1 with a heating jacket 2 and a recirculation cycle and provided with a circulating pump 3 and within which the liquid medium is withdrawn from the reactor 1 at 1a and returned to the reactor 1 at the apex 1b of a conical base 1c of the reactor.

At 5 there is represented a system for monitoring liquid medium to the system in accordance with the desired dosing strategy to maintain the optimum growth and cultivation conditions.

At 6, there is shown an oxygen probe which allows monitoring of the medium for the oxygen partial pressure, this probe representing monitoring of the medium for a variety of parameters.

The withdrawal of material can be effected by an overflow represented at 7 which allows harvesting of product produced by the reactor. A warm water inlet is represented at 2a at the lower part of the jacket 2 and a cool water output is represented at 2b.

The inoculation or addition of support particles is effected directly in the reactor 1 as represented generally at 1d or at 1e in the circulating system, e.g. in the metering line 5.

The fluidized bed has been represented at 8 and consists of carrier particles on which cell growth is formed and is maintained by an upward flow of the recirculated liquid admitted at the base of the reactor 1.

The carriers have a higher specific gravity than the liquid phase and thus are retained within the vessel 1 and continuously agitated therein by the upward flow of the liquid, but are not withdrawn in the circulation unless such removal of the particles is intended. In the latter case, the velocity of flow can be increased to entrain a portion of the particles from the fluidized bed. Normally, however, the particles will be retained in the fluidized bed. Within the cylindrical pipe which forms the reactor and contains the fluidized bed, a coaxial silicon membrane tube 9 is provided through which oxygen is fed to the cells in a bubble free manner. To this end, air or oxygen, generally diluted with $CO_2$, can be fed to an inlet fitting 9a and can pass through the outer space 9b so that oxygen can diffuse through the silicon membrane into the aqueous culture medium immediately surrounding same and thus provide oxygen for the cultivation. At the bottom of the tube 9, the outer space 9b communicates with an inner tube 9c carrying off the exhaust. The oxygation is thus effected in the manner described in German Utility Model DE GM 94 13 576. The silicon membrane which can oxygenation the medium can also be incorporated in the recirculation cycle 4 if desired. In large reactors, a number of such membranes can be provided. The membrane diffusion aeration insures that the cells will not be subjected to any shear stress by bursting gas bubbles and eliminates the need for any antifoaming additives which have been necessary heretofore when bubbling type aeration has been used. The pH value of the growth medium in the vessel is adjusted by variation of the carbon dioxide concentration in the supplied gas phase.

The conical lower end of the reactor has at its upper end the diameter of the reactor 2 which may be some 10 to 30 mm in the case of a conical angle of about 25°, and can converge to the diameter of the recirculating pipe which is generally smaller than 7.5 mm.

The immature hemapoietic cells are completely adherent to the surfaces and in the pores of the carriers. The mature cells tend to release from the carrier and can be discharged through the overflow 7 into a product vessel. In the best mode example of the invention, the carriers are composed of open pore borosilicate glass (SIRAN® of the firm Schott, Mainz, Germany) with a density of about 1.6 Kg/l. The porosity or hollow space ratio is about 50%. The diameters of these glass particles are 400 to 700 $\mu$m and the visibly determined main pore size is about 50 $\mu$m. The cell densities which can be achieved depend upon the cell type but can be between 15 to 200 million cells per ml of the fluidized bed carrier particle packing.

The reactor was continuously operated with a harvested product being carried off at the overflow and with the medium being resupplied to the circulation.

For removal of the carriers, the reactor cover can be opened. Alternatively, a carrier sample extraction system of the type shown in FIG. 5 can be used. In this case, a dip tube 11 can extend below the level of the liquid in the fluidized bed and can be surrounded by a bellows 10 having a variable length of 12 to 23 cm, the tube 11 being composed of polytetrafluoroethylene. In the extended position of the bellows, the Teflon tube 11 is retracted above the reactor medium into the head of the reaction vessel. The tube 11 thus does not interfere with flow characteristics of the reactor. In the contracted position of the bellows, the tube 11 extends into the fluidized bed.

Extraction of the particles is effected by applying suction to the tube end. For this purpose, a flask 12 can be provided in connection with the outer end of the tube 11 and suction can be applied to the flask 12 which can sterilely collect the carriers. Any medium entrained with the particles and any residue of the carriers can be returned via the tube 11 to the reactor. This system allows sterile withdrawal of samples of the carriers from the reactor.

The reactor has, by way of example, the following characteristics:

packing volume of carriers per total volume of the reactor (including recirculation)=0.25 (values between 0.2 and 0.6 are suitable)

packing volume of the carriers=50 ml reactor volume=200 ml membrane area per unit of packing volume (WK=10 $cm^2$/ml)

inoculum: at least $1 \times 10^5$ cells per ml of carrier.

Treatment of Support

The support for the process of the invention is prepared and coated in the following manner:

Cleaning of the glass carriers

One liter of the glass carriers is heated in 1.5 liters of 2.5 m hydrochloric acid for 12 hours at 100° C.

It is then washed twice with 10 liters of high purity water. The carriers are then heated with 1.5 liters of 2.5% nitric acid for 12 hours at 100° C. Thereafter, they are washed twice acid free with 10 liters of high purity water.

Drying

The carriers are dried for 6 to 8 hours at 220° C. in a drying cabinet.

Coating with Gelatin

One liter of the dried carriers is covered with 1.2 liters of dimethyl sulfoxide (DMSO) and then treated with 450 ml of DMSO in which 15 g/l of gelatin has been dissolved. The carriers are shaken in this composition for 3 days at 50° C.

After removal of DMSO and excess gelatin, the carriers are washed 10 times with 10 liters of high purity water heated to a temperature of 60° C.

The carriers are sterilized in an autoclave and introduced into the fluidized bed reactor for cultivation thereon. The gelatin is found to be in a thin layer completely covering the carriers without blocking the pores thereof.

The apparatus used is a 200 ml fluidized bed reactor as shown in FIG. 1 but utilizing external bubble-free aeration, i.e. membrane aeration, in the recirculatory cycle by means of a silicon tube (4 m long corresponding to 0.075 $m^2$ surface area in contact with a culture medium). A biomass probe utilizing capacitance measurement is provided to monitor the biomass density and probes are provided for control of the pH value and the oxygen saturation value of the medium.

The probes are calibrated and the entire reactor is autoclaved. The cooled reactor is filled sterilely with the above described gelatin-coated glass carriers (50 ml piled volume) and subjected to a three day sterility test.

The medium was commercial alpha medium of the firm GIBCO to which 10% fetal calf serum (Boehringer Mannheim, Germany), 2 g/l glucose, 4.3 g/l HEPES and 2.2 g/l $NAHCO_3$ are added. This treatment binds the fibronectin from the calf serum to the gelatin. The sterile reactor is rinsed with the medium to flush out any decomposition products of the medium.

EXAMPLE 1

The reactor prepared as above is inoculated with bone marrow stroma fibroblasts. The inoculum amounted to $3.6 \times 10^7$ cells corresponding to $7.2 \times 10^5$ cells per ml of the carrier.

At day 5, $4 \times 10^6$ peripheral stem cells (corresponding to $8 \times 10^4$ cells per ml of the carrier) were inoculated into the system. One to two medium samples per day were taken from the reactor to determine glucose concentration, lactate concentration and amino acid concentration in the reactor. Every 2 to 3 days, carrier samples were removed for nuclear cell counts by means of the crystal violet-citrate test to determine cell counts on the carriers. The results were compared with the corresponding determinations by means of the biomass capacitance measurements. The results are given in FIG. 2.

Figure 2:
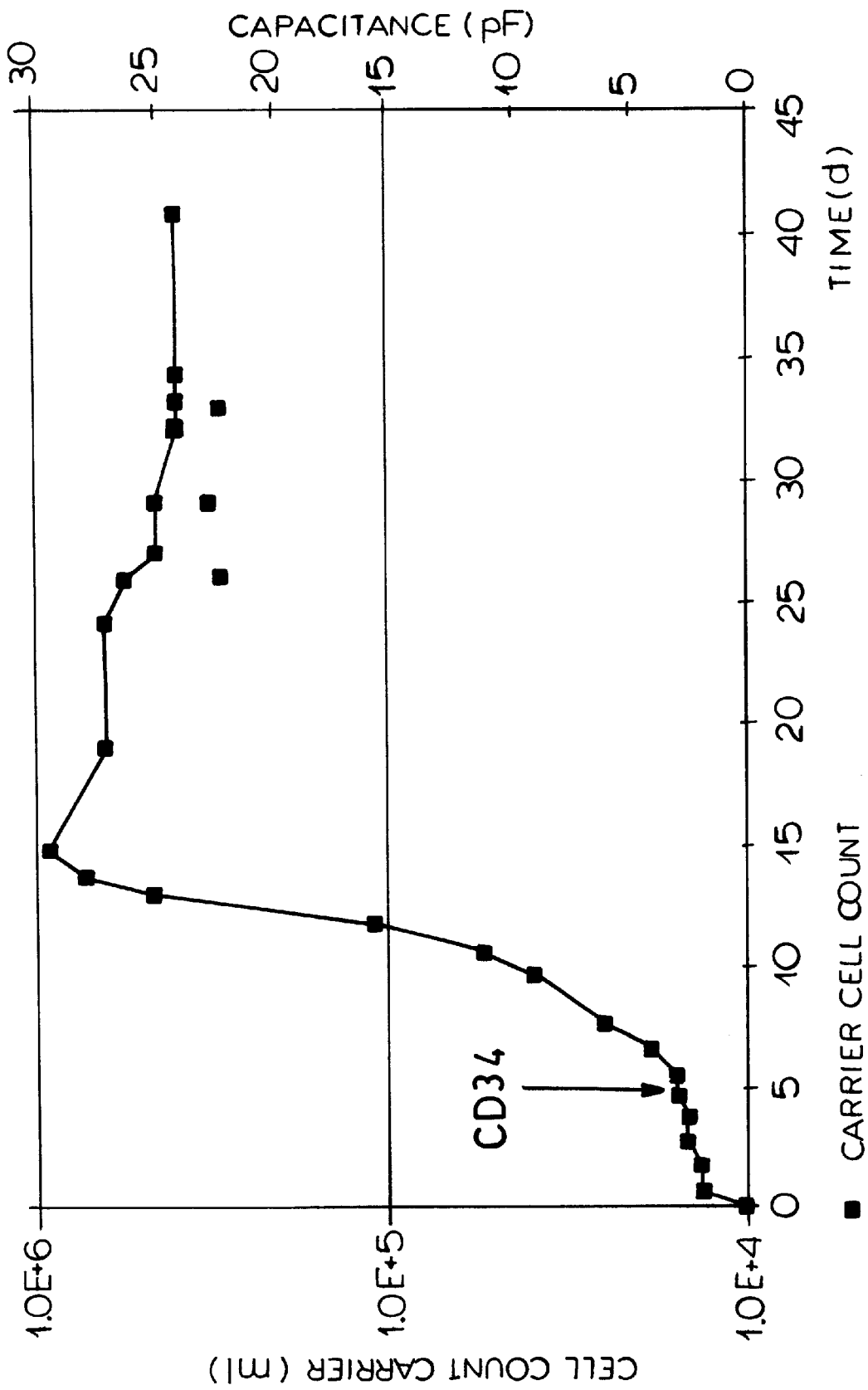
FIG. 2 is a graph in which cell growth is plotted along the ordinate against time along the abscissa and showing also the corresponding measured capacitance for peripheral stem cells immobilized on primary stroma cells utilizing the system of the invention.

From FIG. 2 it will be apparent that there is a practically constant course of the fibroblast concentration on the carriers as well as an exponential increase in the cell count following the addition of the peripheral stem cells (CD 34) and a corresponding increase of the capacitance.

This indicates a satisfactory agreement between the different techniques used in cell count determination.

The exponential increase of the cell count after 14 to 15 days turns into a slow reduction ending in a horizontal branch of the characteristic corresponding to an equilibrium state with a final cell density of 5 to $8 \times 10^5$ cells per ml of carrier and a capacitance value of about 25 pF. A comparison of the equilibrium value to the inoculated quality indicates a 10 fold increase in the cell density.

In parallel to the cell density, the glucose addition and the glucose consumption rate are modified over the period of the investigation. From a starting low dosing and consumption rate in the growth phase of the stroma fibroblasts, after inoculation with stem cells (day 5) there is an increase in the glucose consumption with doubled glucose addition. After 15 days a constant value is obtained also for the glucose consumption rate.

This indicates that the stroma cells are immobilized on the carriers and no significant increase in these cells can be expected. The cell layer on which growth can occur is thus highly stable and enables adhesion of the stem cells. The adhesion and multiplication of the stem cells under differentiation can be indicated by the exponential increase of the cell count. The individual cell types however were not determined.

EXAMPLE 2

Carriers prepared as in Example 1 were used in the described reactor under the aforementioned conditions. In Example 2, the fibroblasts were only precultivated for 12 hours because of time availability. On the thus treated carriers, purified bone marrow, from which the erythrocytes and part of the lymphocytes were removed, was grown. The fluidized bed culture was effected as in Example 1.

Figure 3:
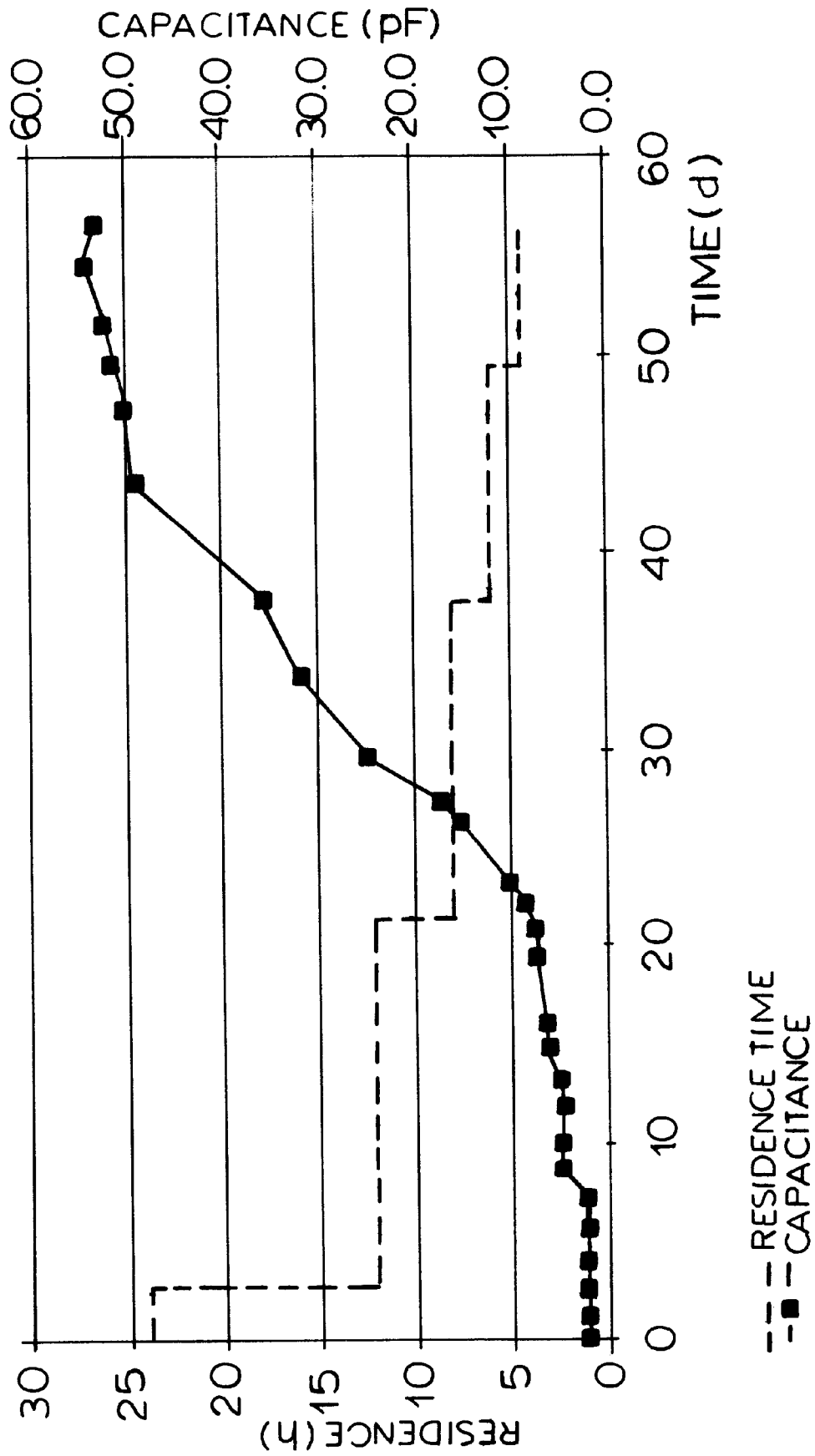
FIG. 3 is a growth curve of the capacitance corresponding to the cell density and the residence time versus time for a culture of purified bone marrow with stroma cells.

FIG. 3 shows the capacity measurement by the biomass probe and the residence period over time. As can be seen from these graphs, the capacitance and the cell count increase slowly, reaching the maximum value in excess of 50 pF after 40 days, corresponding to a cell count in excess of $1 \times 10^6$ cells per ml of the carrier. Based upon the capacitance, the exponential growth of hemapoietic cells can be followed. The residence time of the medium decreases with the increase in cell density and reaches a final value of 4.6 hours.

Figure 4:
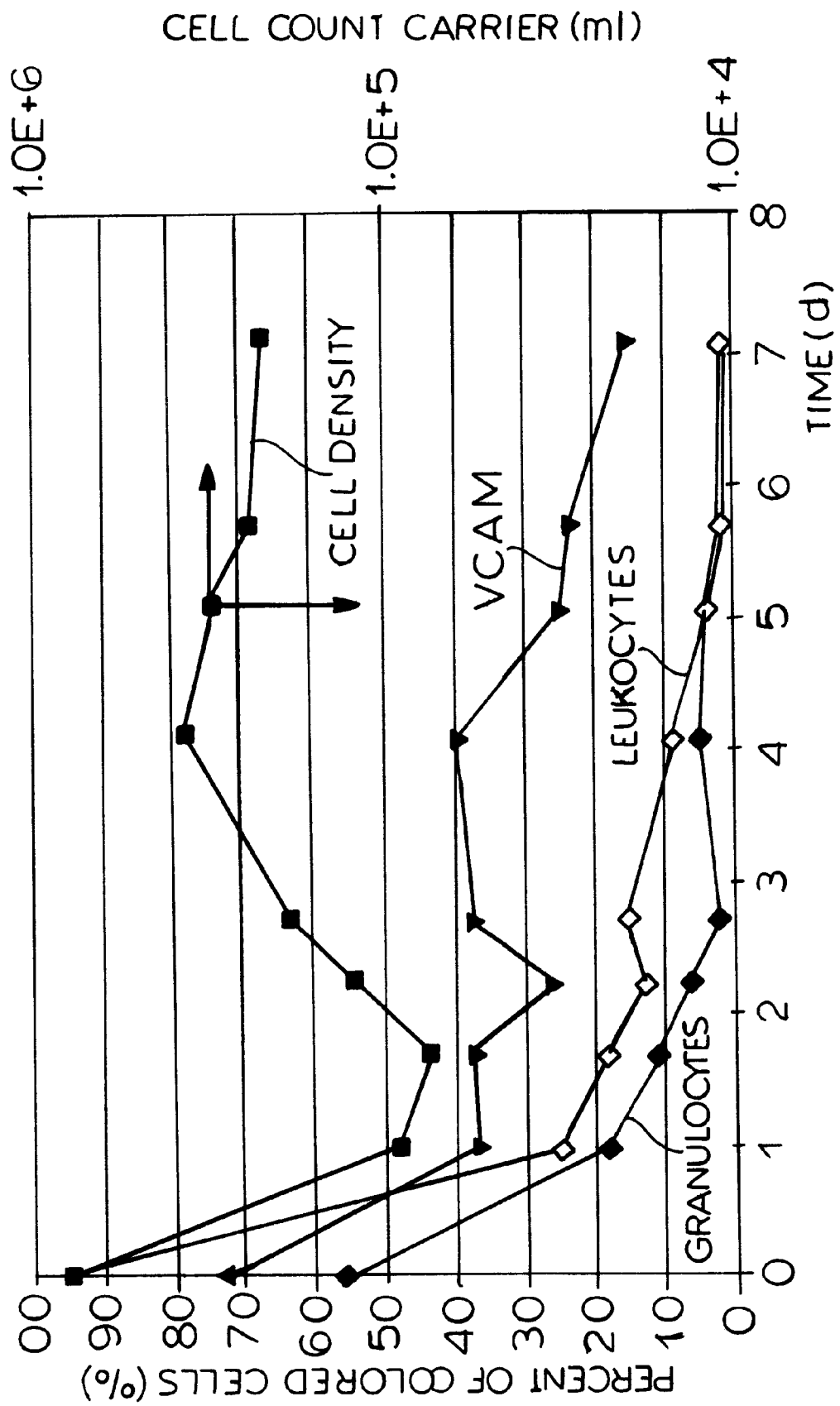
FIG. 4 is a graph of the percentage distribution of the cell types (granulocytes, monocytes, leukocytes and stroma cells) and the cell density versus time.

Furthermore, it can be seen from FIG. 4 that individual cell types can be determined by CD marking based upon Flow Cytomer measurements. This indicates that specific receptors are not expressed over long periods so that only the first days can be used for the cell typing. Cell physiological investigations can also indicate the cell types.

One day after the inoculation of the fluidized bed with the bone marrow, a carrier sample is removed from the reactor and cell typing thereon is undertaken. This indicates that at this stage 40% of the bone marrow progenitor cells (CD 34+and CD 38-and 50% of later progenitor cells (CD 38+) have adhered to the carriers.

Stem cells can not be determined with the Flow Cytometer but form, however, a very small part of the progenitor cells.

By contrast thereto, the more out differentiated cells are immobilized only in a very limited degree, for example, only 8% of all leukocytes and only 15% of the granulocytic cells and the monocytic. The leukocytes include all differentiated white blood cells as well as granulocytes and monocytes. The precultured carrier is also, therefore, suitable for cleaning the progenitor cells out of the bone marrow or blood. This is also indicated by the fact that mainly early hemapoietic cells adhere to the carriers and that only a limited part of the mature blood cells which may limit self replication of the stem cells adhere to the carriers.

TABLE 1 summarizes the results.

TABLE 1

Percentage of the Immobilized Cells Based Upon Inoculum of Bone Marrow

| T-Helper Cells | 0 | T-Suppressor Cells | 8 |
|---|---|---|---|
| Granulocytes | 15 | Monocytes | 15 |
| Early Erythrocytes | 8 | Leukocytes | 8 |
| Early Progenitor Cells | 40 | Later Progenitor Cells | 50 |

Cultivation of peripheral stem cells and of enriched bone marrow without coating of the carrier with stroma cells, gives no results since the hemapoietic cells do not adhere to the carrier.

Figure 6A:
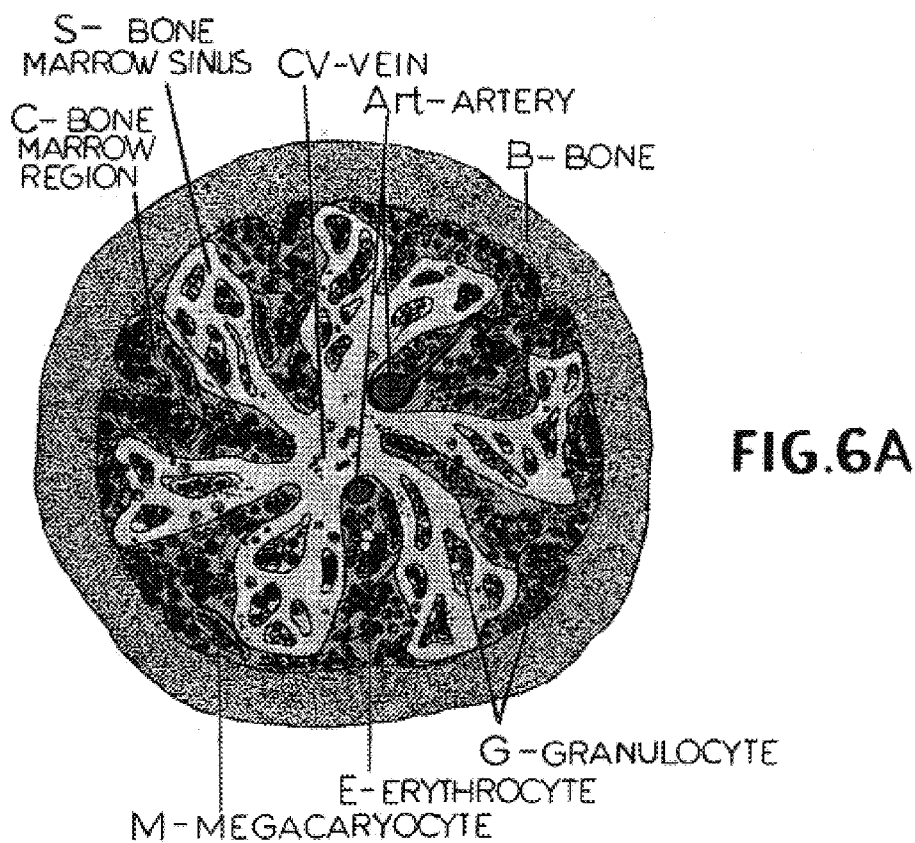
FIG. 6A is a diagram illustrating bone cross section.
Figure 6:
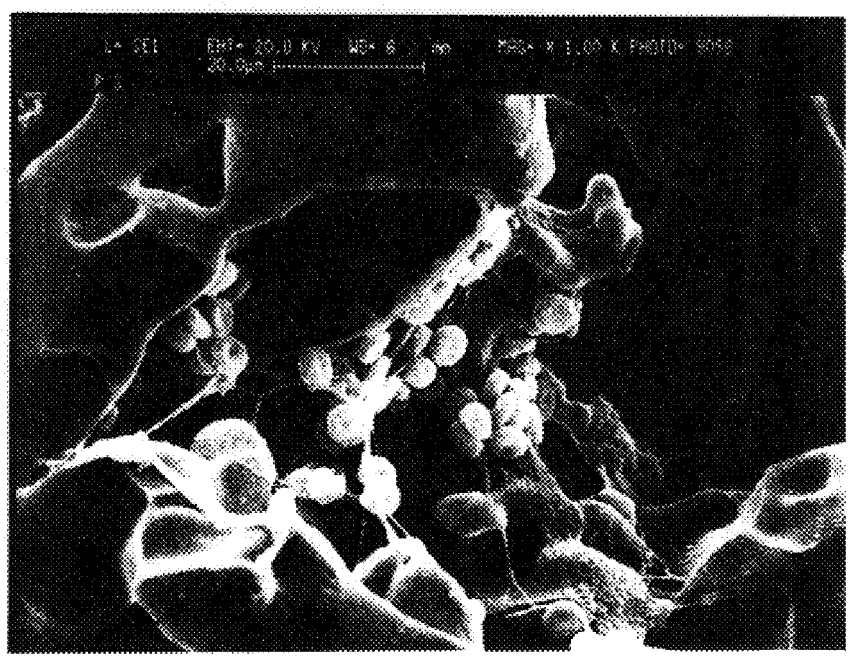
FIG. 6 is a photomicrograph of a macroporous carrier following cell growth.

In FIG. 6A, we have shown a cross section of a bone with the bone marrow contained as compared with the structure of the carrier in the grown state. FIG. 6 shows a photomicrograph. This shows a good agreement between the cell structure on the high porosity carrier and the bone.

EXAMPLE 3

In a further test, only primary stroma cells are cultured in the fluidized bed reactor described in FIG. 1 in order to better characterize the growth supporting cellular layer. The stroma fibroblasts grow slowly upon a doubling of the time to about 130 hours. A maximum cell density of 1 million cells per ml of carrier can be obtained and this can be maintained in excess of 1000 hours substantially constant. The following cytokine concentrations can be determined in the stationary state.

TABLE 2

Median Cytokine Concentrations in Stationary State of the Fermentation:

| PDGF | 10 pg/ml | TGF | 500 pg/ml |
|---|---|---|---|
| G-CSF | >2000 pg/ml | GM-CSF | 1700 pg/ml |
| M-CSF | 7000 pg/ml | MIP la | 135 pg/ml |
| IL-6 | >3000 pg/ml | IL-ll | >3000 pg/ml |
| bFGF | >40 pg/ml | LIF | 1700 pg/ml |

The foregoing results enable the conclusion that stroma fibroblast cells can be cultivated on the carriers in accordance with the invention and, in this form, act as cytokine suppliers. The fibroblast growth enables the adhesion, the growth and the differentiation of pluripotent stem cells.

Figure 5:
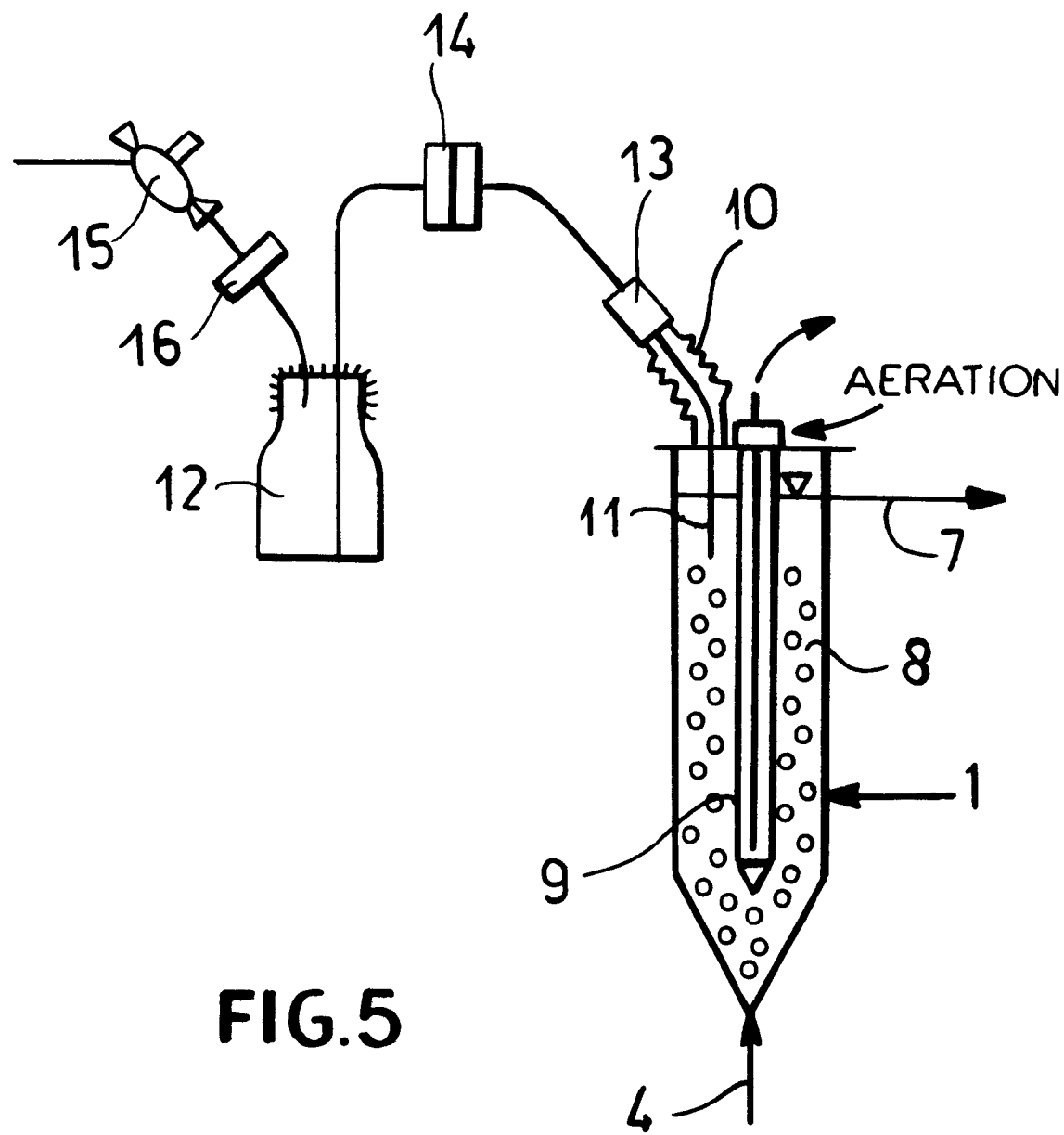
FIG. 5 is a diagram of a sample removal system for the apparatus of FIG. 1.

To recover the stem cells, the carriers with the cells growing thereon are removed by the sampling system shown in FIG. 5, are washed twice with buffer solution and then the cells are removed from the carriers in a 10% trypsin solution. The cells thus liberated are living cells which can be used for any purpose for which cells have been employed in the past. The invention has been used for the cultivation of pluripotent stem cells. Trypsin, when contacted therewith for short periods of time (less than 20 minutes), does not give rise to cell damage.

The Example given as to bone marrow can be repeated for other organ like mixed-cell populations.

For example, liver function cells (hepatocytes) can be immobilized on the carriers treated with the stroma cells and used to replace the liver function of a patient. Furthermore, utilizing this product it is possible to stimulate the decomposition of pharmaceuticals in the liver.

The effect of pharmaceuticals or hormones on thyroid gland simulates can also be investigated in the fluidized bed reactor. The immobilization of osteoblasts on carriers coated with stroma cells is also possible to stimulate their growth and allow production of the osteoblasts in large quantities.

The system shown in FIG. 5 for sampling provides a multiport valve 10 which can be connected to the ambient atmosphere for pressure relief or to a suction source and allows the sample of the carrier bodies to be drawn from the extendable and retractable tube 11 into the vessel 12. A coupling 16 can be provided between the sample vessel 12 and the valve 15. Another coupling 14 can connect a sample vessel to the tube 11 and the bellows 10 can be mounted in a device 13 surrounding the tube 11 and fixed in position on the tube 11.

We claim:

1. A method of cultivating immature human or animal organ-function cells to obtain both mature differentiated cells and progenitor cells, comprising the steps of:

(a) preparing a culture support by coating macroporous glass carriers having a diameter of 200 to 1500 microns, a pore size of 10 to 120 microns and a minimum porosity of about 40% with gelatin, adding the coated carriers to a fluidized bed reactor, adding a culture medium containing an extracellular matrix protein to the fluidized bed reactor whereby the extracellular matrix protein is bound to the gelatin coated on the carriers, adding stromal cells to the fluidized bed reactor containing the carriers coated with gelatin to which the extracellular matrix protein has been bound and culturing the stromal cells in the reactor to immobilize the stromal cells on the coated carriers;

(b) inoculating the culture support formed in step (a) with immature human or animal organ-function cells by adding to the culture medium in the reactor a culture medium containing the immature organ-function cells to suspend the immature organ-function cells in the culture medium in the fluidized bed reactor;

(c) while generating a fluidized bed of the culture support in the culture medium in the fluidized bed reactor recirculating said culture medium from and to said fluidized bed reactor in a recirculation loop;

(d) effecting bubble-free aeration of the culture medium in the fluidized bed to cultivate the immature human or animal organ-function cells on said culture support to obtain both mature differentiated human or animal organ-function cells and progenitor human or animal organ-function cells; and (e) harvesting the mature differentiated human or animal organ-function cells which are released from the culture support from said fluidized bed reactor, while retaining the progenitor human or animal organ-function cells which adhere to the culture support thereby providing an equilibrium between the harvested mature differentiated human or animal organ-function cells, the progenitor cells, and the immature cells added during step (b).

2. The method defined in claim 1 wherein said glass carriers are coated with gelatin and fibronectin and the immobilized stromal cells produced in step (a) are enriched by culturing before inoculation with said organ-function cells.

3. The method defined in claim 2 wherein said culturing is effected with bone marrow stroma cells and the inoculation with organ-function cells is carried out with peripheral stem cells or bone marrow stem cells.

4. The method defined in claim 1 wherein in step (a) the culture medium containing an extracellular matrix protein contains calf serum to provide fibronectin as the extracellular matrix protein.

5. The method defined in claim 1 wherein in step (a) said glass carriers have particle sizes of 400 to 700 microns and a carrier porosity of about 50% and a pore size of 30 to 120 microns.

6. The method defined in claim 1 wherein in step (a) said glass carriers have a porosity of 50 to 75% and the carriers have a volume that is 20 to 60% of the reactor volume.

7. The method defined in claim 1 wherein cultivation of the immature organ-function cells in step (d) is carried out with a continuous controlled supply of said culture medium containing immature organ-function cells in step (b) such that said culture medium has a residence time in said reactor.

8. The method defined in claim 7 wherein said residence time is 10 to 50 h.

9. The method defined in claim 1 further comprising monitoring cell growth of said immature organ-function cells in step (d) on said culture support by measuring capacitance as a measure of biomass and as a measured value of cell count, and controlling feed of said culture medium containing immature organ-function cells in step (b) to said reactor in response to the measured capacitance.

10. The method defined in claim 1 wherein bone marrow function cells are cultivated in said reactor as said immature organ-function cells.

11. The method defined in claim 1 wherein the cultivation of said immature organ-function cells in step (d) is carried out to generate simulated organs.

12. The method defined in claim 1 wherein mature blood cells are produced.

13. A support for cell cultivation comprising macroporous open-pore glass carriers coated with gelatin, treated with fibronectin as an extracellular matrix protein and coated with a layer of stromal cells.

14. The support defined in claim 13 wherein said glass carriers have pore sizes of 30 to 120 microns, diameters of 400 to 700 microns and carrier porosities of about 50%, said carriers having coatings of gelatin on which layers of the fibronectin are applied, said stromal cells being provided on said layers of fibronectin.

15. A method of preparing a carrier for cultivating human or animal organ-function cells, which comprises the steps of:

(a) coating a macroporous glass carrier having a diameter of 200 to 1500 microns, a pore size of 10 to 120 microns and a minimum porosity of about 40% with gelatin; and (b) contacting the coated macroporous glass carrier from step (a) with fibronectin as an extracellular matrix protein whereby the fibronectin is bound to the gelatin coated on the carrier.

16. The method of preparing a carrier for cultivating human or animal organ-function cells defined in claim 15 which further comprises the step of:

(d) following step (b), depositing a stromal cell layer on said macroporous glass carrier thereby forming a culture support.

17. A method for the production of growth and regulatory factors needed for cultivating human or animal organ-function cells, which comprises the steps of:

(a) preparing immobilized stromal cells by coating macroporous glass carriers with a diameter of 200 to 1500 microns having a pore size of 10 to 120 microns and a minimum porosity of about 40% with gelatin, adding the coated carriers to a fluidized bed reactor, adding a culture medium containing an extracellular matrix protein to the fluidized bed reactor whereby the extracellular matrix protein is bound to the gelatin coated on the carriers, adding stromal cells to the fluidized bed reactor containing the carriers coated with gelatin to which the extracellular matrix protein has been bound and culturing the stromal cells in the reactor to immobilize the stromal cells on the coated carriers;

(b) cultivating the stromal cells immobilized on the coated carriers in said reactor in an absence of human or animal organ-function cells to obtain the growth and regulatory factors; and (c) harvesting the growth and regulatory factors obtained according to step (b).

* * * * *